(12) United States Patent
Abraham et al.

(10) Patent No.: US 7,919,533 B2
(45) Date of Patent: Apr. 5, 2011

(54) DIIODOTHYROACETIC ACID AND METHOD OF USE

(76) Inventors: Sal Abraham, Watchung, NJ (US); Ron Kramer, Phoenix, AZ (US)

( * ) Notice: Subject to any disclaimer, the term of this patent is extended or adjusted under 35 U.S.C. 154(b) by 1020 days.

(21) Appl. No.: 10/904,029

(22) Filed: Oct. 20, 2004

(65) Prior Publication Data

US 2006/0083779 A1 Apr. 20, 2006

(51) Int. Cl.
*A61K 31/195* (2006.01)
(52) U.S. Cl. .................................. 514/909; 514/567
(58) Field of Classification Search .................. 424/434
See application file for complete search history.

(56) References Cited

U.S. PATENT DOCUMENTS

| | | | | |
|---|---|---|---|---|
| 3,198,702 A | * | 8/1965 | Hellbaum | 514/570 |
| 4,490,221 A | * | 12/1984 | Collange et al. | 205/435 |
| 4,672,691 A | * | 6/1987 | De Garie et al. | 4/499 |
| 4,673,691 A | * | 6/1987 | Bachynsky | 514/567 |
| 5,910,569 A | | 6/1999 | Latham et al. | |
| 6,380,255 B1 | | 4/2002 | Lavin | |

OTHER PUBLICATIONS

Pittman et al., "Effect of thyroxine analogs on the peripheral metabolism of thyroxine: the half-life and pattern of elimination." Endocrinology (1964), 74 (4), 611-6 (CAPLUS abstract).*
Benedetti, A. "Influence of some thyroxine derivatives on the glycoactive adrenal secretion." Folia Endocrinologica (1961), 14, 253-9 (CAPLUS abstract).*
Beneditti, A. "Influence of some thyroxine derivatives on the glycoactive adrenal secretion" Folia Endrocrinolgica (1961), 14, 253-9 (CAPLUS abstract).*
Pittman, C.S. et al. "Effect of thyroxine analog on the peripheral metabolism of thyoxine: the half life and pattern of elimination" Endocrinology (1964), 74 (4), 611-6.*
Rutgers, et al. Indentification of 3,3-diiodothyroacetic acid sulfate: A major metabolite of 3,3,5-triiodothyronine in propylthiourocil treated rats, 1990, Endocrinology, vol. 124. p. 1617-1624.*
Benedetti, A. Influence of some thyroxine derivatives on the glycoactive adrenal secretion (abstract).*
Pittman, et al. Effects of thyroxine analogs on the periheral metabolism of thyroxine: the half life and pattern of elimination (abstract).*
Rutgers et al. Endocrinology.*
Pittman et al. Endocrinology.*
Rutgers, et al. Identification of 3,3'-diidothyroacetic acid sulfate: A major metabolite of 3,3'5-trithyronine in propylthiouracil treated rats, Endocrinology, vol. 127, No. 4, 1990.*
Marja Rutgers, "Identification of 3,3'-Diodothyroacetic acid sulfate: A major metabolite of 3,3',5-triiodothyronine in Propylthiouracil-treated rats" Endocrinology 1990;p. 1617.
I Várnai, M Farkas: Acta Physiol Hung. Acad. Sci. Hung. 1959; 15: 151-60.
I Várnai, M Farkas, SZ Donhoffer: Acta Physiol Hung. Acad. Sci. Hung. 1959; 16: 197-201.
M Rutgers, FA Heusdens, F Bonthuis and TJ Visser. Endocrinology. Jul. 1989;125(1):433-43.
M Rutgers, FA Heusdens, TJ Visser. Endocrinology. Jul. 1989;125(1):424-32.
O'Connell, M. et al, "Changes in serum concentrations of 3,3',5'-thriiodothyronine and 3,5,3'-triiodothyronine during prolonged moderate exercise," J Clin Endocrinol Metab. Aug. 1979, V.49(2), pp. 242-246.
Epstein, Y. et al.,"Serum 3,5,3'-triiodothyronine and 3,3',5'-triiodothyronine concentrations during acute heat load," J Clin Endocrinol Metab. Nov. 1979, V. 49(5), pp. 677-678.
"Sur le metabolisme de la 3:3':5'-triiodothyronine," Biochimica et Biophysica Acta. Dec. 1956, V.22 (3), pp. 550-557.
"Inhibition of Thyroxine Action By 3,3',5'-Triiodothyronine," Endocrinology, V. 64 (3), pp. 466-468.
"Metabolic effects of thyroid hormone derivatives," Thriod, Feb. 2008, (2), pp. 239-253.
Pittman et al., "Biological Activity of 3,3',5'-Triiodo-DL-Thyronine," Endocrinology, V. 70 (1), pp. 79-83.
Sachs, Marvin L., "Abnormalities of cholesterol metabolism in hypothyroidism and the effects of treatment with thyroid hormones and thyroxin analogues," Journal of Chronic Diseases, Nov. 1961, V. 14 (5), pp. 515-536.

* cited by examiner

*Primary Examiner* — Anand U Desai
*Assistant Examiner* — Melissa S Mercier
(74) *Attorney, Agent, or Firm* — Booth Udall, PLC

(57) ABSTRACT

The present invention relates to a method of administering an effective amount of a diiodothyroacetic acid in order to shift the proportion between lean body mass and adipose tissue in favor of lean body mass in human individuals.

15 Claims, No Drawings

DIIODOTHYROACETIC ACID AND METHOD OF USE

BACKGROUND OF INVENTION

Over recent years obesity has reached epidemic proportions. Obesity contributes to more than 300,000 deaths each year and according to federal guidelines, half the population is overweight and a third is obese. Obesity is defined as an excess proportion of total body fat correlating with a body weight greater than 20 percent of ideal body weight (IBW). Body Mass Index (BMI) is another method to determine whether or not an individual is obese. BMI utilizes a mathematical equation consisting of weight and height measurements in order to determine total body fat. A BMI between 25-29.9 indicates an individual is overweight. Causes for obesity include genetic, environmental, economic, emotional, and physiological factors. These factors can then lead to the over consumption of total calories. The amount of total calories consumed versus the amount of total calories burned determines the amount of fat stored for energy reserves. Calories or Kcals (kilocalories) are defined as the amount of heat necessary to raise the temperature of 1 gram of water 1 degree Celsius. The amount of total calories burned is defined as the calories utilized by exercise plus basal metabolic rate (BMR) or resting metabolic rate (RMR). BMR represents the amount of calories needed to maintain IBW at rest. Increasing BMR results in fewer calories stored as fat and can promote weight loss if the amount calories burned is greater than the amount of calories ingested. One of the main factors that controls BMR is the percentage of lean body weight.

Standard medical therapy for obesity includes oral prescription medications. Most of these medications are designed to regulate appetite by releasing serotonin or catecholamine. For instance Sanorex, Mazanor, Adipex-P, and Meridia are common appetite suppressant medications. However most of these medications can only be used on a short term basis and are scheduled as controlled substances due to the fact that they can become addictive. Other side effects include increased heart rate, blood pressure, constipation and insomnia. Merida is the only appetite suppressant that has been approved for long term use. Another long term pharmaceutical approach to weight loss is the fat absorption inhibitor Xenical. Xenical works by blocking about 30 percent of dietary fat from being absorbed. Enzymes in the digestive system, called lipases, assist in the digestion of dietary fats. Xenical attaches to the lipases and inhibits the digestion of dietary fat as triglycerides into absorbable free fatty acids and monoglycerides, which are then excreted in the bowel. Xenical literature recommends not ingesting more than 30 percent of total calories from dietary fat per day due to concerns regarding loose bowels. It appears that a common and unpleasant side effect of Xenical includes flatulence and loose bowels when a high fat diet is consumed during Xenical treatment.

The previously mentioned weight control methods do not take into account the importance of maintaining or increasing the lean body mass in the process of weight loss. Medical methods to decrease body fat often contribute to the catabolic wasting of lean body mass. Increased lean body mass enhances metabolism and helps in losing fat weight, as well as maintaining the accomplished weight reduction. Diminished lean body mass decreases metabolism and results in difficulties in maintaining healthy body weight. An ideal weight management approach should be to reduce body weight to acceptable levels by restoring the optimal proportions of fat to lean body mass. By maintaining or increasing the lean body mass while simultaneously reducing body fat, the weight loss regimen would serve the general purpose of improving the overall health of the individual.

The present invention relates to a method of administering an effective amount of an iodothyroacetic acid analog in order to shift the proportion between lean body mass and adipose tissue in favor of lean body mass in a human individual. Iodothyronines traditionally have been utilized to treat thyroid disorders such as hypo and hyper thyroidism. The most common iodothyronines consist of tetraiodothyronine (T4), triiodothyronine (T3), diiodothyronine (T2), and monoiodothyronine (T1) but also include the acetic acid analogs Tetraiodothyroacetic Acid (TETRAC or TA4) and Triiodothyroacetic Acid (TRIAC or TA3). We purpose for the first time that the use of diiodothyroacetic acid (TA2) is novel and unobvious due to its ability to shift the proportion between lean body mass and adipose tissue in favor of lean body mass without causing sympathomimetic stimulation, loose bowel or addictive symptomology commonly associated with obesity related prescription and over the counter medications. This unobvious function can also increase the variables associated with physical performance for the regulation of athletic function in humans.

The thyroid gland, in response to stimulation by TSH, produces 3,5,3',5'-tetratiodothyronine (T4), T3, and reverseT3. The synthesis of these hormones requires the amino acid tyrosine and the trace mineral iodine. Within the cells of the thyroid gland, iodide is oxidized to iodine by hydrogen peroxide, a reaction termed the organification of iodide. Iodine then binds to the number 3 position in the tyrosyl ring in a reaction catalyzed by the thyroid peroxidase enzyme, a reaction yielding 3-monoiodotyrosine (MIT). A subsequent addition of another iodine to the number 5 position of the tyrosyl residue on MIT creates 3,5-diiodotyrosine (DIT). T4 is created by the condensation or coupling of two DIT molecules. Within the thyroid, smaller amounts of DIT can also condense with MIT to form either T3 or reverseT3.

Iodothyronines have been patented for a number of applications. For instance, U.S. Pat. No. 4,673,691 by Bachynsky demonstrates a method for inducing human weight loss. U.S. Pat. No. 5,910,569 by Latham et al. describes a method for the use of iodothyronine polymers for the treatment of thyroid disorders. U.S. Pat. No. 6,380,255 by Lavin et al. describes a method for the treatment of dermal skin atrophy using thyroid hormone compounds.

The iodothyroacetic acid analogs utilized in this invention consist of all isomers, esters, salts, ethers, metabolites and analogs of diiodothyroacetic acid. This naturally occurring acetic acid analog is a direct metabolite of triiodothyronine (T3) and triiodothyroacetic acid (Triac) as demonstrated in Endocrinology October 1990; 127(4): 1617-24 and Endocrinology July 1989; 125(1): 424-32. It should be understood that this invention is not construed as limited in scope by the details contained therein, as it is apparent to those skilled in the art that modification in materials and methods can be made without deviating from the scope of the invention.

U.S. Pat. No. 4,673,691 by Bachynsky describes a method for human weight reduction with 2,4-dinitrophenol and a thyroid hormone. The dinitrophenol is administered to elevate body temperature, while the thyroid preparation is utilized maintain T3 levels that were present at the onset of the treatment. This invention represents an improvement in standard weight loss preparations due to the combination of dinitrophenol and T3. This combination represents an improvement in the use of dinitrophenol for weight loss although dinitrophenol is toxic and may lead to adverse reactions. U.S. Pat. No. 4,673,691 by Bachynsky addresses weight loss while the present invention focuses on shifting the proportion between lean body mass and adipose tissue in favor of lean body mass. This combination represents an improvement in the use of dinitrophenol for weight loss although dinitrophenol is toxic and may lead to adverse reactions.

U.S. Pat. No. 5,910,569 by Latham et al. describes a method for the synthesis of various iodothyronine polymers for use in the treatment of thyroid disorders. Since these iodothyronine polymers are released by digestive proteolysis it is expected that they would have a long physiologic effect because of the sustained release from the polymers of the monomeric thyroid hormones and thus give stable, consistent pharmaceutical compositions for the treatment of thyroid hormone deficiencies. This combination represent an improvement in the use of iodothyronines for the treatment of thyroid hormone deficiencies although these polymers do not address the use of diiodothyroacetic acid to shift the proportion between lean body mass and adipose tissue in favor of lean body mass.

U.S. Pat. No. 6,380,550 by Lavin describes a method for treating dermal atrophy of the skin. Lavin has found that topical application of a composition comprising at least one thyroid hormone compound or thyroid hormone-like compound in a pharmacologically acceptable base is effective in treating dermal atrophy of the skin. It also provides an improved cosmetic appearance to aging, atrophied, steroid-affected, or sun damaged skin. This combination represents a novel and unobvious use of iodothyronines for the treatment of dermal atrophy of the skin although this invention does not address the use of diiodothyroacetic acid to shift the proportion between lean body mass and adipose tissue in favor of lean body mass.

SUMMARY OF INVENTION

The present invention relates to a method of administering an effective amount of an iodothyroacetic acid in order to shift the proportion between lean body mass and adipose tissue in favor of lean body mass in a human individual. This unobvious function can also increase the variables associated with physical performance for the regulation of athletic function in humans. The method comprises administering to humans an effective amount of a composition consisting of an iodothyroacetic acid such as but not limited to all isomers, esters, salts, ethers, metabolites and analogs of 3,3' diiodothyroacetic acid and 3,5 diiodothyroacetic acid.

Diiodothyroacetic acid exerts a direct enhancement of metabolic rate via an increase in oxygen consumption and body temperature. This increase in metabolic rate results in an enhancement of the utilization of orally consumed nutrients. 3,3' diiodothyroacetic acid is a precursor to T3, Triac, and T2. Small increases in T3 result in increased protein synthesis for muscle tissue accretion. Thus the said compound can be given to humans either in conjunction with or without a high protein diet (1.25 to 1.8 grams protein/kilogram of body weight) and proper anaerobic training program in order to shift the proportion between lean body mass and adipose tissue in favor of lean body mass for the regulation body weight.

DETAILED DESCRIPTION

The chemical term iodothyroacetic acid may refer to but is not limited to 3,3' diiodothyroacetic acid and 3,5 diiodothyroacetic acid. Possible alternatives include all isomers, esters, salts, ethers, metabolites and analogs of diiodothyroacetic acid. This invention concerns a diiodothyroacetic acid and all previously mentioned alternatives. The previous examples of various diiodothyroacetic acids are presented by way of illustration only. It should be understood that this invention is not construed as limited in scope by the details contained therein, as it is apparent to those skilled in the art that modifications in materials and methods can be made without deviating from the scope of the invention.

The iodoamino acids TA4 and TA3 are products of deamination and oxidative decarboxylation of T4 and T3 and have been detected in serum by direct RIA measurements. Reported mean concentrations in the serum of healthy adults have been 8.7 nanograms per deciliter and 2.6 nanograms per deciliter for TA3 and 28 nanograms per deciliter for TA4. Serum TA4 levels are reduced during fasting and in patients with severe illness, although the percentage of conversion of T4 to TA4 is increased. The concentration of serum TA3 remains unchanged during the administration of replacement doses of T4 and T3. It has been suggested that intracellular rerouting of T3 to TA3 during fasting is responsible for the maintenance of normal serum TSH levels in the presence of low T3 concentrations.

The sulfate conjugate 3,3'-diiodothyroacetic acid (3,3'-TA2S) was discovered in plasma, and occasionally in bile, of 6-propyl-2-thiouracil-treated rats after administration of T3 as shown in Endocrinology October 1990; 127(4): 1617-24. The significant plasma 3,3'-TA2S levels, even in unanesthetized animals, illustrate the physiological relevance of this T3 metabolite. Diiodothyroacetic acid is a direct naturally occurring metabolite of T3, Triac, and T2, which has never been investigated or sold as a new drug therefore it may be sold as a dietary supplement.

The biosynthetic pathway of diiodothyroacetic acid is unique in that it possesses several direct pathways to different thyroid hormones in contrast to other acetic acid analogs such as T3A and T4A. Diiodothyroacetic acid has direct reversible pathways to T3, Triac and T2. The ability to increase the levels of these different thyroid hormones is one aspect of diiodothyroacetic acid uniqueness. The other aspect is its ability to shift the proportion between lean body mass and adipose tissue in favor of lean body mass via small increases in T3 for enhanced protein synthesis and muscle tissue accretion.

Without being bound to any theory, effective administration of diiodothyroacetic acid shifts the proportion between lean body mass and adipose tissue in favor of lean body mass due to its location in the thyroid biosynthetic pathway. Diiodothyroacetic acid exerts a direct enhancement of metabolic rate via an increase in oxygen consumption and body temperature. This increase in metabolic rate results in an enhancement of the utilization of orally consumed nutrients. Diiodothyroacetic acid acts as a precursor hormone resulting in specific small increases in T3, Triac, and T2. Small increases in T3 facilitate protein synthesis for muscle anabolism. In the present method of promoting lean body mass, diiodothyroacetic acid should be administered in a daily dose of from about 1 mcg to about 6 mg. It is preferred that the daily dose be divided into a plurality of individual doses. It is further preferred that three to six individual doses be used. In any case, the individual doses are preferably from about 100 mcg to about 1 mg each. After every 4 weeks of continual use, a 2-week cessation period is recommended. Thus the said compound can be given to humans either in conjunction with or without a high protein diet (1.25 to 1.8 grams protein per kilogram of body weight) and proper anaerobic training program in order to shift the proportion between lean body mass and adipose tissue in favor of lean body mass for the purpose of body weight regulation.

After an extensive review of the scientific literature and previous patents regarding the ability of diiodothyroacetic acid to alter body composition, it then became the focus of this invention that all isomers, esters, salts, ethers, metabolites and analogs of diiodothyroacetic acid could be administrated perorally as an effective means to shift the proportion between lean body mass and adipose tissue in favor of lean body mass in humans. The oral daily doses can be between 1 mcg to 6 mg per day. The preferred daily dosing schedule should be divided into 3-6 sub dose applications per day in order maintain adequate blood hormone concentrations. In addition to peroral use, several other routes including transdermal, sublingual, intranasal, and parenteral administration may be effectively utilized.

What is claimed is:

1. A method of promoting lean body mass in a human individual having a body mass index of at least 25, comprising directly administering to the individual an effective amount of diiodothyroacetic acid.

2. The method of claim 1, wherein the diiodothyroacetic acid comprises one of 3,3' diiodothyroacetic acid and 3,5 diiodothyroacetic acid.

3. The method of claim 1, wherein the diiodothyroacetic acid is selected from the group consisting of diiodothyroacetic acid isomers, esters, salts, and ethers thereof.

4. The method of claim 1, wherein administration is selected from the group comprising peroral, transdermal, sublingual, intranasal, and parenteral administration.

5. The method of claim 1, wherein the diiodothyroacetic acid is administered in a daily dose in a range of about 1 microgram to about 6 milligrams.

6. A method of increasing a proportion of lean body mass to adipose tissue in a human individual having a body mass index of at least 25, comprising directly administering to the individual an effective amount of diiodothyroacetic acid.

7. The method of claim 6, wherein the diiodothyroacetic acid comprises one of 3,3' diiodothyroacetic acid and 3,5 diiodothyroacetic acid.

8. The method of claim 6, wherein the diiodothyroacetic acid is selected from the group consisting of diiodothyroacetic acid isomers, esters, salts, and ethers thereof.

9. The method of claim 6, wherein administration may be selected from the group comprising peroral, transdermal, sublingual, intranasal, and parenteral administration.

10. The method of claim 6, wherein the diiodothyroacetic acid is administered in a daily dose in a range of about 1 microgram to about 6 milligrams.

11. A dietary supplement comprising diiodothyroacetic acid.

12. The composition of claim 11, wherein the diiodothyroacetic acid comprises one of 3,3' diiodothyroacetic acid and 3,5 diiodothyroacetic acid.

13. The composition of claim 11, wherein the diiodothyroacetic acid is selected from the group consisting of diiodothyroacetic acid isomers, esters, salts, and ethers thereof.

14. The composition of claim 11, wherein administration is selected from the group comprising peroral, transdermal, sublingual, intranasal, and parenteral administration.

15. The composition of claim 11, wherein the diiodothyroacetic acid is administered in a daily dose in a range of about 1 microgram to about 6 milligrams.

* * * * *